(12) United States Patent
Usuda

(10) Patent No.: US 8,294,890 B2
(45) Date of Patent: Oct. 23, 2012

(54) METHOD AND DEVICE FOR INSPECTING DEFECTS ON BOTH SURFACES OF MAGNETIC DISK

(75) Inventor: Katsutoshi Usuda, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 252 days.

(21) Appl. No.: 12/855,915

(22) Filed: Aug. 13, 2010

(65) Prior Publication Data

US 2011/0075133 A1  Mar. 31, 2011

(30) Foreign Application Priority Data

Sep. 30, 2009 (JP) ................. 2009-227196

(51) Int. Cl.
*G01N 21/00* (2006.01)
(52) U.S. Cl. ................. 356/237.2; 356/237.5
(58) Field of Classification Search ..... 356/237.1–237.5
See application file for complete search history.

(56) References Cited

U.S. PATENT DOCUMENTS 5,416,594 A * 5/1995 Gross et al. ............... 356/237.5
6,809,809 B2 * 10/2004 Kinney et al. ............. 356/237.5
2004/0012775 A1 * 1/2004 Kinney et al. ............. 356/237.2

FOREIGN PATENT DOCUMENTS

| JP | 3-186739 A | 8/1991 |
| JP | 5-21561 A | 1/1993 |
| JP | 6-118015 A | 4/1994 |
| JP | 8-22619 A | 1/1996 |
| JP | 2009-175121 A | 8/2009 |

* cited by examiner

*Primary Examiner* — Michael P Stafira
(74) *Attorney, Agent, or Firm* — Mattingly & Malur, PC

(57) ABSTRACT

A device that is capable of simultaneously inspecting both sides of surfaces of a magnetic disk to detect defects thereon includes a front-side defect detecting section and a back-side defect detecting section each of which optically detect a scratch and a defect that are present on the front and back surfaces of the magnetic disk, to improve a throughput for inspection. The back-side defect detecting section has an optical path changing section that reflects a laser beam emitted by a laser light source to change an optical path thereof and thereby to direct the laser beam toward the back surface of the magnetic disk and that reflects scattered light that has been collected by a Fresnel lens to change an optical path thereof and thereby to direct the scattered light toward a first photoelectric converter.

9 Claims, 3 Drawing Sheets

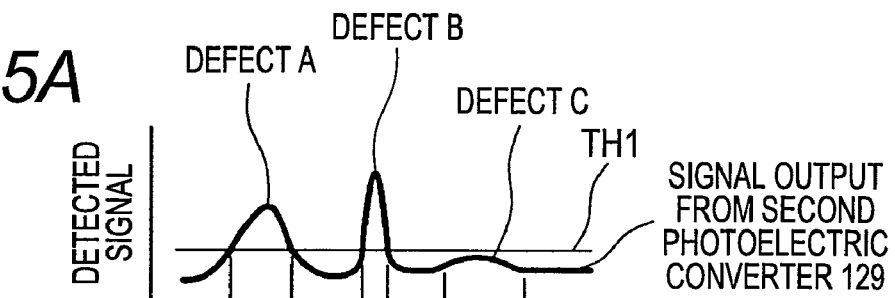
FIG. 5A
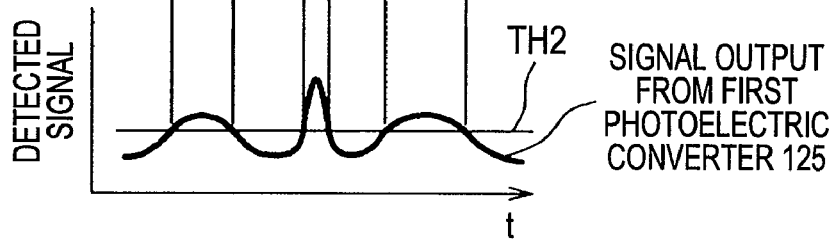
FIG. 5B
FIG. 6
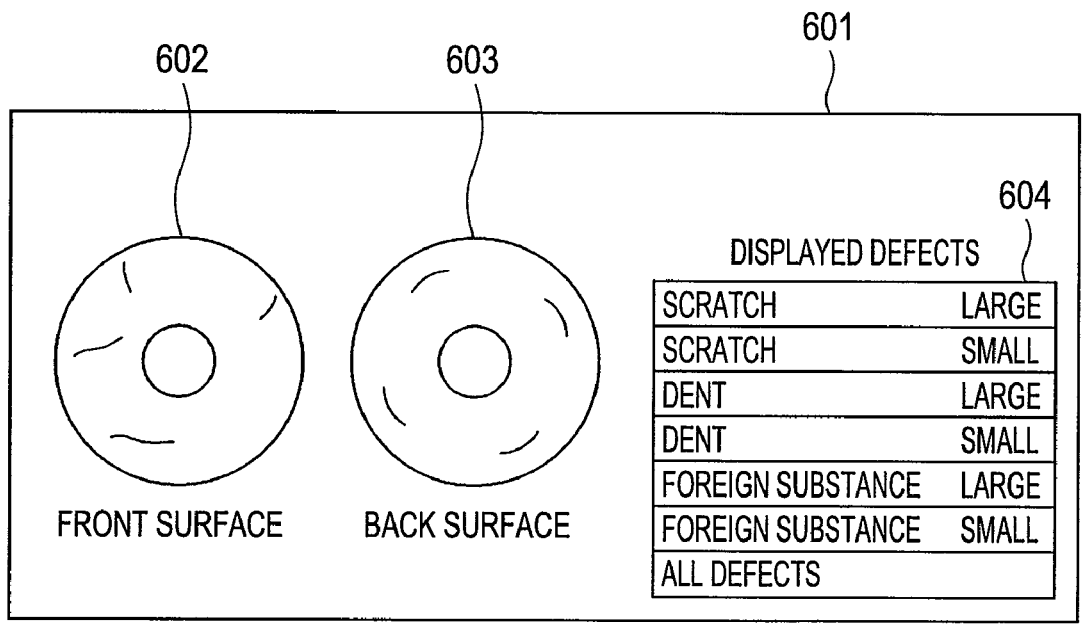

METHOD AND DEVICE FOR INSPECTING DEFECTS ON BOTH SURFACES OF MAGNETIC DISK

BACKGROUND OF THE INVENTION

1. Field of the Invention

The present invention relates to a method and device for inspecting front and back surfaces of a magnetic disk for defects thereon. The invention more particularly relates to a method and device for inspecting front and back surfaces of a magnetic disk for defects thereon, which are suitable to optically inspect the front and back surfaces of the magnetic disk simultaneously and thereby to detect a dent and a scratch on the front and back surfaces of substrates of the magnetic disk and detect foreign substances attached to the front and back surfaces of the magnetic disk.

2. Description of the Related Art

A device for optically inspecting a magnetic disk for microscopic defects on surfaces of a substrate thereof is needed to have more enhanced inspection sensitivity and higher throughput for inspection. Schemes of achieving higher throughput for inspection are described in JP-A-H3-186739 and JP-A-H5-21561. Specifically a laser light source is used to increase the intensity of illumination light and a high-sensitivity sensor detects light reflected on and scattered from a substrate. However, if the intensity of the light emitted is too high, the surface of the substrate may be damaged. Thus, it is necessary to irradiate the substrate with light having a controlled intensity and detect, with the maximum sensitivity, reflected and scattered light from a defect that is present on the surface of the substrate by irradiating the substrate with light having a limited intensity. JP-A-H5-21561 describes a structure that includes a photomultiplier as a structure that allows reflected and scattered light to be detected with the maximum sensitivity.

JP-A-H6-118015 describes an inspection system for an increase in the throughput. This inspection system includes a substrate reversing mechanism located between a front surface inspecting section that inspects the front surface of a magnetic disk and a back surface inspecting section that inspects the back surface of the magnetic disk. The inspection system sequentially inspects the front and back surfaces of the magnetic disk, thereby improving the throughput for inspection.

In addition, JP-A-H8-22619 describes an inspection system that uses a handling device to transfer a magnetic disk between multiple types of magnetic disk inspection devices and performs a series of inspections on the magnetic disk. In the inspection system, one of inspecting sections, which optically inspects a foreign substance, optically inspects front and back surfaces of the magnetic disk simultaneously.

In addition, JP-A-2009-175121 describes a structure for irradiating both surfaces of a disk with light simultaneously for defect inspection.

Scattered light from a microscopic defect has characteristics such that the smaller the size of a defect is, the less the amount (per unit area) of light scattered from the defect, and the scattered light spreads over the whole space above the defect. Thus, in order to detect the microscopic defect with high sensitivity by means of light having the same intensity, it is necessary to efficiently collect the light scattered from the defect in a larger region and thereby to detect the defect.

In order to collect the scattered light in the larger region, the size of an objective lens that is used to collect light scattered from a substrate is increased and the size of the numerical aperture of the objective lens is increased. It is, however, necessary to prevent the objective lens from interfering with other parts of an inspection device when the objective lens is installed in the inspection device. Thus, practically, increasing the size of the numerical aperture by increasing the size of the objective lens has a limit.

Generally, an inspection device has a mechanism for maintaining and driving the substrate on the side of the back surface of the substrate. Thus, the inspection device has a narrow space for an optical system on the side of the back surface of the substrate.

It is, therefore, difficult to provide the same optical system (that is used for inspection) on the side of the back surface of the substrate as that provided on the side of the front surface of the substrate, when inspections on both surfaces of a substrate are simultaneously to be performed.

In addition, when the size of the numerical aperture is increased by increasing the size of the objective lens, it is necessary to increase the size of a focusing lens that is used to focus light (scattered light) collected by the objective lens onto a detection surface of a detector. Since the lens group is increased in size, a lens barrel that holds the lens group is also increased in size. Thus, the optical system for inspection is also increased in size. It is, therefore, difficult to reduce the size and weight of the inspection device.

JP-A-H3-186739 and JP-A-H5-21561 do not consider that, for improvement in inspection sensitivity for a defect, the size of the numerical aperture of an objective lens is increased without increasing the size of the inspection device for increasing the amount of scattered light (to be detected) relative to the amount of emitted light.

In the method (described in JP-A-H6-118015) for inspecting the surfaces of a magnetic disk for defects thereon, the magnetic disks are sequentially transferred between the two inspecting sections so that the defects that are present on the front and back surfaces of the magnetic disk are inspected and the throughput for inspection of both surfaces of the magnetic disk is improved.

However, since the two inspecting sections are arranged side by side and the reversing mechanism is provided between the two inspecting sections, an area on which to install the inspection system will be large.

In addition, JP-A-H8-22619 describes that the front and back surfaces of the magnetic disk are optically inspected simultaneously. However, a specific structure for optically inspecting the surfaces simultaneously is not disclosed.

In addition, JP-A-H4-62457 describes that a structure including light sources and a camera is provided on each side of the front and back surfaces of a disk and optically inspects both surfaces of the disk simultaneously for defects thereon. The light sources are provided on both sides of the disk in bilateral symmetry with respect to the central axis of the disk and emit light on one surface of the disk in an oblique direction. However, JP-A-H4-62457 does not describe a structure that uses an optical system having a large numerical aperture on both sides of the disk to detect light scattered from microscopic defects.

SUMMARY OF THE INVENTION

The present invention provides a method and device for inspecting both surfaces of a magnetic disk for defects thereon, which are capable of solving the aforementioned problems in the conventional techniques and detecting microscopic defects with high sensitivity without increasing the size of the device.

According to the present invention, a detection optical system includes aspherical Fresnel lenses to reduce the size of the device and allow the device to inspect both surfaces of the magnetic disk simultaneously for defects thereon. The device is capable of detecting microscopic defects with high sensitivity without increasing the size of the device.

According to an aspect of the present invention, a device for inspecting both surfaces of a magnetic disk for defects thereon includes: a table unit that is capable of rotating and moving the magnetic disk with the magnetic disk mounted thereon; a front-side defect detecting section that optically detects a scratch and a defect that are present on a front surface of the magnetic disk placed on the table unit; a back-side defect detecting section that optically detects a scratch and a defect that are present on a back surface of the magnetic disk; a processing section that processes an inspection result obtained by the front-side defect detecting section and an inspection result obtained by the back-side defect detecting section; and an output section that outputs the inspection results processed by the processing section.

In the device for defect inspection, the back-side defect detecting section includes: a laser light source that emits a laser beam; a light collecting section having a Fresnel lens that collects scattered light, exclusive of regularly reflected light, both of the light being included in reflected light from the back surface of the magnetic disk that has been irradiated with the laser beam emitted by the laser light source; a first photoelectric converter that detects the scattered light that has been collected by the light collecting section; and an optical path changing section that reflects the laser beam emitted by the laser light source to change an optical path thereof and thereby to direct the laser beam toward the back surface of the magnetic disk and that reflects the scattered light that has been collected by the Fresnel lens included in the light collecting section to change an optical path thereof and thereby to direct the scattered light toward the first photoelectric converter.

In addition, according to another aspect of the present invention, a method for inspecting both surfaces of a magnetic disk for defects thereon includes the steps of: irradiating front and back surfaces of the magnetic disk mounted on a table with laser beams, the table rotating and moving in one direction with the magnetic disk mounted thereon; detecting a scratch and a defect that are present on the front surface of the magnetic disk by receiving and processing light that is reflected from the front surface that has been irradiated with the laser beam; and detecting a scratch and a defect that are present on the back surface of the magnetic disk by receiving and processing light that is reflected from the back surface that has been irradiated with the laser beam.

In the method, the step of detecting a scratch and a defect that are present on the back surface further includes the substeps of: causing the laser beam emitted by a laser light source to be reflected on a first surface of a prism to change an optical path thereof and direct the laser beam toward the back surface of the magnetic disk; irradiating the back surface of the magnetic disk with the laser beam whose optical path has been changed; causing light scattered from the back surface of the magnetic disk that is irradiated with the laser beam to pass through a Fresnel lens and to be focused; causing the scattered light that has passed through the Fresnel lens to be reflected on a second surface of the prism to change an optical path thereof and direct the scattered light toward a first photoelectric converter; detecting, by using the first photoelectric converter, the scattered light whose optical path has been changed; detecting, by using a second photoelectric converter, light regularly reflected on the back surface of the magnetic disk; and processing a signal obtained by causing the first photoelectric converter to detect the scattered light and processing a signal obtained by causing the second photoelectric converter to detect the regularly reflected light, so as to detect a scratch and a defect that are present on the back surface of the magnetic disk.

According to the present invention, since the detection optical system includes the aspherical Fresnel lenses to reduce the size of the system, it allows the device to inspect simultaneously both surfaces of a magnetic disk for defects thereon. The device is capable of detecting microscopic defects with high sensitivity without increasing the size of the device.

In addition, according to the present invention, since inspection for defects on both surfaces of a magnetic disk can be simultaneously performed by using the device that can be installed in a space whose area is half or less than that for a conventional inspection device, inspection with high cost performance can be achieved with a high throughput for inspection.

These features and advantages of the invention will be apparent from the following more particular description of a preferred embodiment of the invention, as illustrated in the accompanying drawings.

BRIEF DESCRIPTION OF THE DRAWINGS

FIG. 5A is a graph showing an example of a waveform of a signal output from a second photoelectric converter that has detected light regularly reflected on a region of a front surface of a sample.

FIG. 5B is a graph showing an example of a waveform of a signal output from a first photoelectric converter that has detected light scattered from the region of the front surface of the sample.

FIG. 6 is a front view of a display screen that shows an example of inspection results formed using a graphic user interface.

DESCRIPTION OF THE PREFERRED EMBODIMENTS

According to the present invention, an optical system includes an aspherical Fresnel lens and is used instead of a detection optical system having a conventional lens, in order to detect a microscopic defect with high sensitivity. The optical system is included in a structure that simultaneously inspects both surfaces of a sample. The aspherical Fresnel lens allows the optical system to be installed in a relatively narrow space and to have a large numerical aperture.

In addition, according to the present invention, a device for inspecting both surfaces of a magnetic disk for defects thereon includes: a front-side defect detecting section for optically detecting a scratch and a defect that are present on the front surface of the magnetic disk; and a back-side defect detection section for optically detecting a scratch and a defect that are present on the back surface of the magnetic disk. The back-side defect detecting section includes an optical path changing section. The optical path changing section reflects a laser beam emitted by a laser light source to change an optical path thereof and thereby to direct the laser beam toward the back surface of the magnetic disk. Also, the optical path changing section reflects scattered light that has been collected by the Fresnel lens to change an optical path thereof and thereby to direct the scattered light toward a first photoelectric converter.

Thus, the defect inspection device is capable of optically detecting a defect that is present on the back surface of the magnetic disk even when a space on the side of the back surface of the magnetic disk is narrow. The following describes an example of the device for inspecting defects on both surfaces of a magnetic disk with reference to the accompanying drawings.

Figure 1:
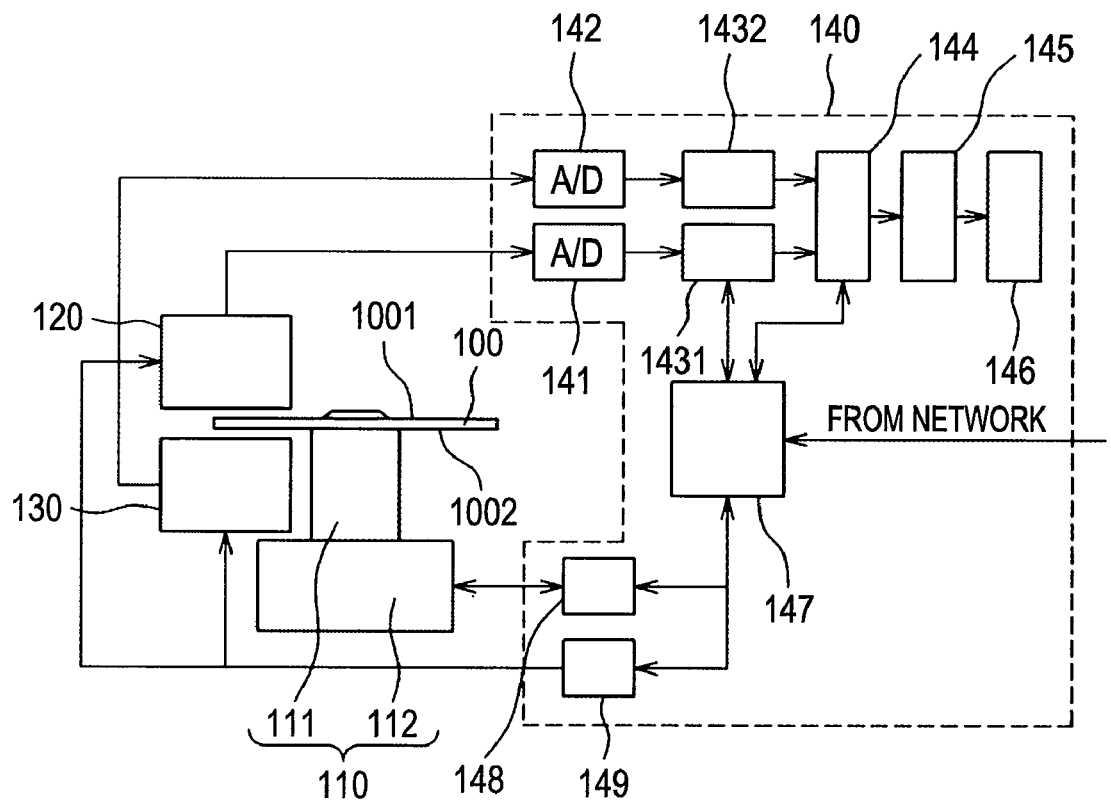
FIG. 1 is a block diagram showing an outline configuration of a device for inspecting a front surface of a disk for a defect thereon.

FIG. 1 is a diagram showing the entire configuration of the device for inspecting both surfaces of a magnetic disk for defects thereon according to an embodiment of the present invention. The defect inspection device includes a table unit 110, a front-side inspection optical system 120, a back-side inspection optical system 130 and a signal processing and control system 140. A sample 100 that is to be inspected is placed on the table unit 110. The table unit 110 includes a table 111 and a stage 112. The table 111 is capable of rotating with the sample (magnetic disk) 100 placed thereon. The stage 112 is capable of moving in a direction perpendicular to a main axis of the rotation of the table 111. The table unit 110 also includes a chuck mechanism (not shown) that holds the sample 100 by means of a chuck.

Figure 2:
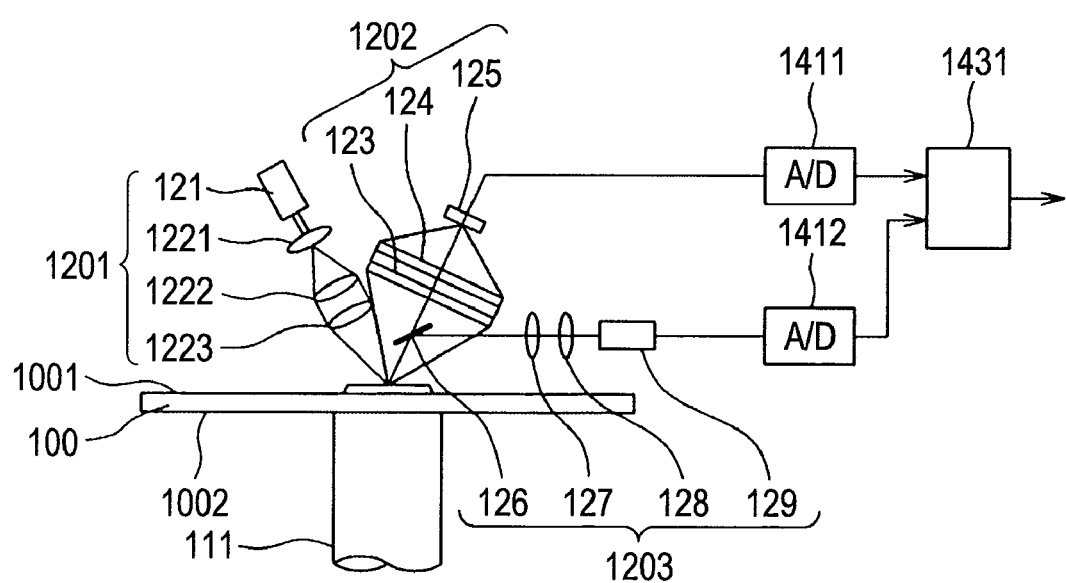
FIG. 2 is a front view of an outline configuration of an inspection optical system that is arranged on the side of the front surface of the disk.

FIG. 2 is a diagram showing an outline configuration of the front-side inspection optical system 120 that detects a defect that is present on the side of the front surface 1001 of the sample 100. The front-side inspection optical system 120 includes an illumination system 1201, a scattered light detection optical system 1202 and a regularly reflected light detection optical system 1203.

The front-side scattered light illumination system 1201 includes a first laser light source 121, a magnifying lens 1221, a collecting lens 1222 and a focusing lens 1223. The magnifying lens 1221 magnifies a laser beam emitted by the first laser light source 121. The collecting lens 1222 collects the magnified laser beam. The focusing lens 1223 focuses the collected laser beam onto the front surface of the sample 100.

The front-side scattered light detection optical system 1202 includes a first aspherical Fresnel lens 123, a second aspherical Fresnel lens 124, and a first photoelectric converter 125 (e.g., an avalanche photodiode (APD) or a photomultiplier tube (PMT)). The first aspherical Fresnel lens 123 corresponds to an objective lens that collects scattered light that is included in reflected light (regularly reflected light and the scattered light) from the front surface of the sample 100. The second aspherical Fresnel lens 124 corresponds to a focusing lens that focuses the scattered light that has been collected by the first aspherical Fresnel lens 123. The first photoelectric converter 125 detects, with high sensitivity, the scattered light that has been focused by the second aspherical Fresnel lens 124.

The front-side regularly reflected light detection optical system 1203 includes a mirror 126, a collecting lens 127, an imaging lens 128, and a second photoelectric converter 129 (e.g., a photodiode array that has a plurality of pixels). The mirror 126 reflects the regularly reflected light that is included in the reflected light (including regularly reflected light and scattered light) from the sample 100 to change an optical path of the regularly reflected light.

The collecting lens 127 collects the regularly reflected light whose optical path has been changed by the mirror 126. The imaging lens 128 images the regularly reflected light that has been collected by the collecting lens 127. The second photoelectric converter 129 detects an image of the regularly reflected light that has been imaged by the imaging lens 128. The mirror 126 is formed in a sufficiently small shape so as not to reflect the light (scattered light) exclusive of the regularly reflected light.

Figure 3A:
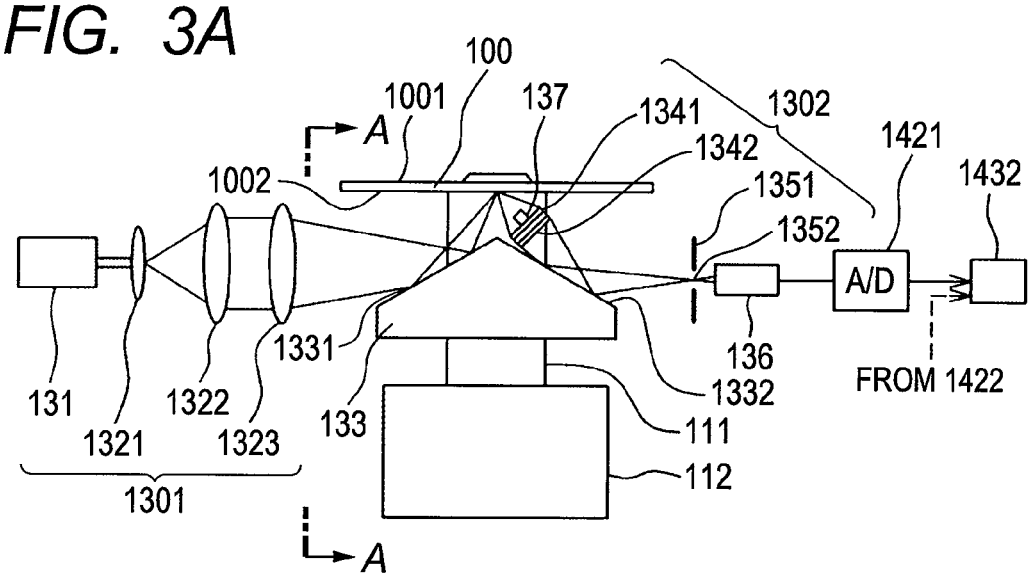
FIG. 3A is a front view of an outline configuration of an inspection optical system that is arranged on the side of a back surface of the disk.
Figure 3B:
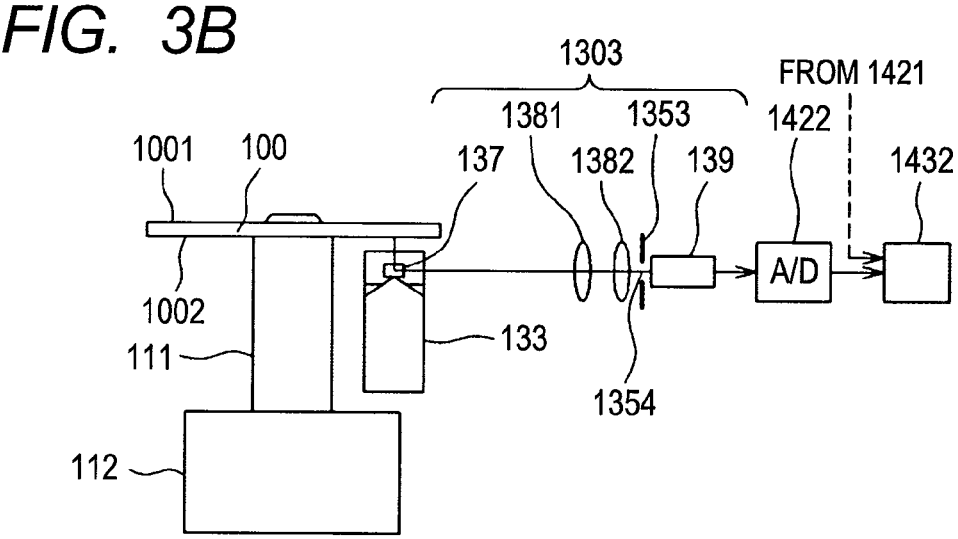
FIG. 3B is a side view of the inspection optical system, taken along line A-A of FIG. 3A.

FIGS. 3A and 3B show an outline configuration of the back-side inspection optical system 130 that detects a defect that is present on the side of the back surface 1002 of the sample 100. The back-side inspection optical system 130 includes an illumination system 1301, a scattered light detection optical system 1302 and a regularly reflected light detection optical system 1303.

The illumination system 1301 of the back-side inspection optical system 130 includes a second laser light source 131, a magnifying lens 1321, a collecting lens 1322, a focusing lens 1323 and a prism 133 as shown in FIG. 3A. The magnifying lens 1321 magnifies a laser beam emitted by the second laser light source 131.

The collecting lens 1322 collects the magnified laser beam. The focusing lens 1323 focuses the collected laser beam onto the back surface of the sample 100. The prism 133 changes an optical path of the laser beam that has passed through the focusing lens 1323. Since the prism 133 changes the optical path of the laser beam, the second laser light source 131 can be installed in a position separately from a relatively narrow space that is located under the sample 100.

Thus, the inspection on the side of the back surface 1002 of the sample 100 can be performed, without a significant change in the configuration of the table unit of a conventional device that inspects only on one surface of a sample for defects thereon.

The back-side scattered light detection optical system 1302 includes a third aspherical Fresnel lens 1341, a fourth aspherical Fresnel lens 1342, a pinhole plate 1351 and a third photoelectric converter 136 (e.g., a avalanche photodiode (APD) or a photomultiplier tube (PMT)). The third aspherical Fresnel lens 1341 corresponds to an objective lens that collects scattered light that is included in light reflected from the back surface 1002 of the sample 100 that has been illuminated with the laser beam. The fourth aspherical Fresnel lens 1342 corresponds to a focusing lens that focuses the scattered light that has been collected. The pinhole plate 1351 includes a pinhole 1352.

The scattered light passes through the fourth aspherical Fresnel lens 1342, then the optical path thereof is changed by the prism 133, and the scattered light passes through the pinhole 1352. The pinhole plate 1351 blocks stray light exclusive of the scattered light. The third photoelectric converter 136 detects, with high sensitivity, the scattered light that has passed through the pinhole 1352 of the pinhole plate 1351.

Since the back-side scattered light detection optical system 1302 includes the aspherical Fresnel lenses, the scattered light detection optical system 1302 can be installed in a position separately from the relatively narrow space that is located under the sample 100. In addition, the prism 133 changes the optical path of the scattered light that will be detected.

Thus, without a significant change in the configuration of the table unit of the conventional device that inspects only on one surface of a sample for defects thereon, the inspection on the side of the back surface 1002 of the sample 100 can be performed.

The back-side regularly reflected light detection optical system 1303 includes a mirror 137, a collecting lens 1381, an imaging lens 1382, a fourth photoelectric converter 139 (e.g., a photodiode array having a plurality of pixels) and a pinhole plate 1353. The mirror 137 changes an optical path of the regularly reflected light that is included in the reflected light (including regularly reflected light and scattered light) from the back surface 1002 of the sample 100 that has been illuminated with the laser beam. The mirror 137 reflects the regularly reflected light to cause the light to propagate in a direction perpendicular to the surface of the sheet of FIG. 3A. The collecting lens 1381 collects the regularly reflected light whose optical path has been changed by the mirror 137. The imaging lens 1382 forms an image of the regularly reflected light that has been collected by the collecting lens 1381.

The fourth photoelectric converter 139 detects the formed image of the regularly reflected light. The pinhole plate 1353 is arranged between the imaging lens 1382 and the fourth photoelectric converter 139. The regularly reflected light that passes through the imaging lens 1382 passes through the pinhole plate 1353. The pinhole plate 1353 having a pinhole 1354 blocks stray light exclusive of the regularly reflected light.

Figure 4A:
FIG. 4A is a cross sectional view of a normal aspherical lens.
Figure 4B:
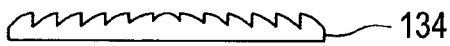
FIG. 4B is a cross sectional view of an aspherical Fresnel lens having the same numeral aperture as the aspherical lens shown in FIG. 4A.

FIG. 4A shows a normal aspherical optical lens 1340, and FIG. 4B shows an example of an aspherical Fresnel lens 134 having the same numerical aperture as the optical lens 1340. As is apparent from FIGS. 4A and 4B, the aspherical lens 134 can be formed in a relatively thin shape, compared with the normal aspherical optical lens 1340 having the same numerical aperture as the aspherical Fresnel lens 134. In the present embodiment, the aspherical lens included in the scattered light detection optical system has such characteristics as the aspherical Fresnel lens 134.

The aspherical Fresnel lens may be made of normal optical glass. In addition, the aspherical Fresnel lens may be made of plastic. When the aspherical Fresnel lens is made of plastic, it can be processed and formed in any shape. In addition, when the material of the aspherical Fresnel lens is plastic, the weight of the aspherical Fresnel lens is low. Therefore, when the plurality of aspherical Fresnel lenses, each of which is processed and formed in a predetermined shape, are combined and used in an inspection optical system, a lens barrel that holds the lenses does not need to have high strength, compared with a lens barrel that holds normal glass lenses. Thus, the lens barrel that holds the lenses made of plastic can be formed in a relatively slim structure.

Referring to FIG. 1, the signal processing and control system 140 includes a first A/D converter 141, a second A/D converter 142, a first signal processing section 1431, a second signal processing section 1432, an integrated signal processing section 144, a storage section 145, an output section 146, an entire system controller 147, a table controller 148, and an inspection optical system controller 149.

The first A/D converter 141 performs analog-to-digital conversion on a detected signal from the front-side inspection optical system 120 and amplifies the converted signal. The second A/D converter 142 performs analog-to-digital conversion on a detected signal from the back-side inspection optical system 130 and amplifies the converted signal.

The first signal processing section 1431 receives the signal from the first A/D converter 141 and processes the received signal. The second signal processing section 1432 receives the signal from the second A/D converter 142 and processes the received signal. The integrated signal processing section 144 integrates the signal processed by the first signal processing section 1431 with the signal processed by the second signal processing section 1432 and processes the integrated signal. The storage section 145 stores the result processed by the integrated signal processing section 144. The output section 146 has a display screen and outputs, to the display screen, the result processed by the integrated signal processing section 144.

The entire system controller 147 controls the entire signal processing and control system 140. The table controller 148 receives a control signal from the entire system controller 147 and controls the table section 110 on the basis of the received control signal. The inspection optical system controller 149 receives a control signal from the entire system controller 147 and controls the front-side inspection optical system 120 and the back-side inspection optical system 130 on the basis of the received control signal.

Next, operations of each section are described. A load mechanism (not shown) places the sample 100 onto the table 111 of the table unit 110. While the chuck mechanism (not shown) holds the sample 100 on the table, the table controller 148 controls the table unit 110 so that the table unit 110 rotates the table 111 and moves the stage 112 in synchronization with the rotation of the table 111 in the direction perpendicular to the main axis of the rotation of the table 111.

While the sample 100 is rotated and moved by the table unit 110, the inspection optical system controller 149 controls the front-side inspection optical system 120 and the back-side inspection optical system 130 to operate the first laser light source 121 and the second laser light source 131 so that each of the first and second laser light sources 121 and 131 emits a laser beam.

In the front-side inspection optical system 120, the magnifying lens 1221 magnifies the laser beam so that the diameter of the laser beam emitted by the first laser light source 121 is increased as shown in FIG. 2. The collecting lens 1222 collects the magnified laser beam. The focusing lens 1223 focuses the collected laser beam onto the front surface 1001 of the sample 100 so that the laser beam is incident on the front surface 1001 at an angle of approximately 30 degrees.

From the front surface 1001 of the sample 100 irradiated with the focused laser beam, light (including regularly reflected light and scattered light) is reflected according to a defect such as a scratch and a microscopic dent or roughness of the surface. In this case, the scattered light is distributed according to the size of the defect that is present on the front surface 1001. Specifically, when the defect such as a scratch is large, the light scattered from the large defect has a relatively high intensity and is distributed with directivity.

When the defect (such as a scratch) is small, the light scattered from the small defect has a relatively low intensity and is isotropically distributed.

The first aspherical Fresnel lens 123 corresponds to the objective lens that collects the scattered light that is included in the reflected light (regularly reflected light and scattered light) from the front surface 1001 of the sample 100. A part of the light reflected from the front surface 1001 of the sample 100 is incident on the first aspherical Fresnel lens 123. The first aspherical Fresnel lens 123 is installed in a position such that a focal point thereof coincides with a point of irradiation with the laser beam on the front surface 1001. The first aspherical Fresnel lens 123 collects the reflected light and changes the collected light to parallel light. The parallel light is output from the first aspherical Fresnel lens 123.

The regularly reflected light, which is a part of the reflected light that propagates toward the first aspherical Fresnel lens 123, is reflected by the mirror 126 before reaching the first aspherical Fresnel lens 123. Accordingly, the mirror 126 changes the optical path of the regularly reflected light so that the regularly reflected light is not incident on the first aspherical Fresnel lens 123.

The light, which is scattered from the sample 100 and incident on and collected by the first aspherical Fresnel lens 123 and output as the parallel light from the Fresnel lens 123, is incident on the second aspherical Fresnel lens 124 and focused onto a focal point of the second aspherical Fresnel lens 124.

The first photoelectric converter 125 is arranged so that the focal point of the second aspherical Fresnel lens 124 is located on a detection surface of the first photoelectric converter 125. The first photoelectric converter 125 detects the light that has been scattered from the sample 100 and focused by the second aspherical Fresnel lens 124, and obtains a signal on the basis of the detected light.

The signal obtained by the first photoelectric converter 125 is received by an A/D converter 1411 that is included in the A/D converter 141. The A/D converter 1411 converts the received signal into a digital signal and amplifies the digital signal. After that, the amplified digital signal is received by the front-side detected signal processing section 1431.

On the other hand, the light, which is regularly reflected from the sample 100 and then reflected on the mirror 126 so that the optical path of the light is changed, is incident on the collecting lens 127 and changed to parallel light. The collecting lens 127 is installed in a position such that a focal point thereof corresponds with a point of incidence of the laser beam on the sample 100. The parallel light is output from the collecting lens 127 and incident on the imaging lens 128.

The regularly reflected light that has been incident on the imaging lens 128 is then output therefrom to form an image of the regularly reflected light on an image surface of the imaging lens 128. The second photoelectric converter 129 is arranged so that a detection surface of the second photoelectric converter 129 coincides with the image surface of the imaging lens 128. Thus, the second photoelectric converter 129, which is composed of a photodiode array having a plurality of pixels or the like, detects the image of the regularly reflected light.

A signal of the image of the regularly reflected light detected by the second photoelectric converter 129 is received by an A/D converter 1412 that is included in the A/D converter 141. The A/D converter 1412 converts the received signal into a digital signal and amplifies the digital signal. The amplified digital signal is received by the front-side detected signal processing section 1431.

The front-side detected signal processing section 1431 receives the detected signals from the first and second photoelectric converters 125 and 129 and processes the detected signals to detect a defect that is present on the front surface 1001 of the sample 100.

FIG. 5A shows an example of the waveform of a signal output from the second photoelectric converter 129 that has detected light regularly reflected on a region of the front surface 1001 of the sample 100.

FIG. 5B shows an example of the waveform of a signal output from the first photoelectric converter 125 that has detected light scattered from the region of the front surface 1001 of the sample 100.

For example, in a case of defect A in which a part of the signal waveform of the second photoelectric converter 129 has a value that is higher than a first threshold Th1, a part of the signal waveform of the first photoelectric converter 125 has a value that is higher than a second threshold Th2, and both of the parts have wide bottoms, the defect is determined to be a scratch that is present on the sample.

In a case of defect B in which a part of the signal waveform of the second photoelectric converter 129 has a value that is higher than the first threshold Th1, a part of the signal waveform of the first photoelectric converter 125 has a value that is higher than the second threshold Th2, and both of the parts have narrow bottoms, the defect is determined to be a foreign substance.

In a case of defect C in which a part of the signal waveform of the second photoelectric converter 129 has a value that is lower than the first threshold value Th1, a part of the signal waveform of the first photoelectric converter 125 has a value that is higher than the second threshold Th2, and both of the parts have relatively wide bottoms, the defect is determined to be a dent of the sample.

In addition, the first signal processing section 1431 determines the size (e.g., large size, medium size or small size) of each of detected defects by using information on the number of pixels of the image of the regularly reflected light imaged by the second photoelectric converter 129. The results determined by the first signal processing section 1431 and information on the position of each of the defects are transmitted to the integrated signal processing section 144.

In the back-side inspection optical system 130, the second laser light source 131 emits a laser beam, and the magnifying lens 1321 magnifies the laser beam so that the diameter of the laser beam is increased. Then, the laser beam having the increased diameter is collected by the collecting lens 1322 and changed to parallel light by the collecting lens 1322. The laser beam then passes through the focusing lens 1323.

After that, the laser beam is reflected on a surface 1331 of the prism 133 so that the optical path thereof is changed. Then, the laser beam is focused onto the back surface 1002 of the sample 100 that is located above a focal point of the focusing lens 1323. The surface 1331 of the prism 133 is set so that the laser beam reflected on the surface 1331 is incident on the back surface 1002 of the sample 100 at a predetermined angle (of approximately 30 degrees).

Light (including regularly reflected light and scattered light) is reflected on the back surface 1002 of the sample 100 that has been irradiated with the focused laser beam. A part of the reflected light is incident on the third aspherical Fresnel lens 1341 that is arranged so that a focal point thereof coincides with a point of irradiation with the laser beam on the back surface 1002. The third aspherical Fresnel lens 1341 corresponds to the objective lens that collects light scattered from the back surface 1002 of the sample 100. The light is collected by the third aspherical Fresnel lens 1341 and changed to parallel light by the third aspherical Fresnel lens 1341.

Then, the parallel light is output from the third aspherical Fresnel lens 1341. A part of the light directed toward the third aspherical Fresnel lens 1341, which is regularly reflected on the back surface 1002, is reflected on the mirror 137 before reaching the third aspherical Fresnel lens 1341 so that an optical path of the light is changed. Therefore, the light reflected on the mirror 137 is not incident on the third aspherical Fresnel lens 1341.

The light which is scattered from the back surface 1002 of the sample 100 and incident on and collected by the third aspherical Fresnel lens 1341 is changed to be a parallel light. The parallel light is then incident on the fourth aspherical Fresnel lens 1342. After that, the scattered light passes through the fourth aspherical Fresnel lens 1342 is then reflected on a surface 1332 of the prism 133 so that the optical path of the light is changed. Then, the scattered light is focused onto a focal point of the fourth aspherical Fresnel lens 1342. The surface 1332 of the prism 133 is inclined at a certain angle so that the scattered light that is reflected on the surface 1332 propagates in a predetermined direction (parallel to the back surface 1002 of the sample 100).

In the present embodiment, the back-side illumination system 1301 is set so that the laser beam emitted by the second laser light source 131 propagates in a direction parallel to the back surface 1002 of the sample 100 until the laser beam reaches the surface 1331 of the prism 133. Also, in the present embodiment, the surfaces 1331 and 1332 of the prism 133 are inclined at the same angle. Each of the surfaces 1331 and 1332 of the prism 133 may be made of a mirror.

The pinhole plate 1351 is arranged at the focal point of the fourth aspherical Fresnel lens 1342. The light that is scattered from the sample 100 and focused onto the focal point of the fourth aspherical Fresnel lens 1342 passes through the pinhole 1352 of the pinhole plate 1351. Most of the light (reflected on optical parts such as the prism 133, i.e., stray light), exclusive of the scattered light, cannot pass through the pinhole 1352 and is blocked by the pinhole plate 1351. Thus, most of the light detected by the third photoelectric converter 136 is the light that has been scattered from the back surface 1002 of the sample 100 and has passed through the pinhole 1352.

The third photoelectric converter 136 detects the light scattered from the back surface 1002 of the sample 100 and obtains a signal of the detected light. The signal is input to the A/D converter 1421 that is included in the A/D converter 142. The A/D converter 1421 converts the signal into a digital signal and amplifies the digital signal. The amplified signal is input to the back-side detected signal processing section 1432.

The light, which is regularly reflected from the sample 100 and reflected by the mirror 137 so that the optical path thereof is changed, is incident on the collecting lens 1381. The collecting lens 1381 is arranged so that a focal point thereof coincides with a point of irradiation with the laser beam on the back surface 1002 of the sample 100. The regularly reflected light is changed to parallel light by the collecting lens 1381. The parallel light is output from the collecting lens 1381 and incident on the imaging lens 1382.

The regularly reflected light that is incident on the imaging lens 1382 is output from the imaging lens 1382. Then, the regularly reflected light passes through a pinhole 1354 that is formed in the pinhole plate 1353 so that the stray light is blocked by the pinhole plate 1353. After that, the image of the regularly reflected light is formed on an image surface of the imaging lens 1382. The fourth photoelectric converter 139 is arranged so that the image surface of the imaging lens 1382 coincides with a detection surface of the fourth photoelectric converter 139. Thus, the fourth photoelectric converter 139, which is composed of a photodiode array having a plurality of pixels or the like, detects the image of the regularly reflected light.

A signal of the image of the regularly reflected light detected by the fourth photoelectric converter 139 is input to the A/D converter 1422 included in the A/D converter 142. The A/D converter 1422 converts the signal into a digital signal and amplifies the digital signal. Then, the amplified signal is input to the back-side detected signal processing section 1432.

The back-side detected signal processing section 1432 processes the signal transmitted from the third photoelectric converter 136 and the signal transmitted from the fourth photoelectric converter 139 to detect a defect that is present on the back surface 1002 of the sample 100. In a similar manner to the signal processing (described above) performed by the front-side detected signal processing section 1431, the back-side detected signal processing section 1432 compares the signal detected by the third photoelectric converter 136 with a threshold and compares the signal detected by the fourth photoelectric converter 139 with a threshold to determine the size and type of the defect. Then, the back-side detected signal processing section 1432 transmits the results of the determination and information on the position of the defect to the integrated signal processing section 144.

According to the present embodiment, detecting scattered light from a smaller defect can be achieved compared with a conventional technique. For example, a detection optical system that includes a conventional optical lens cannot detect a defect that is smaller than several hundred nanometers in size. However, defects of approximately 100 nanometers can be detected by means of the detection optical systems according to the present embodiment while both surfaces of the sample are inspected.

According to the present embodiment, combination of the aspherical Fresnel lenses constitutes the compact detection system having a high numeral aperture. Thus, the defect inspection device is capable of detecting microscopic defects on both surfaces of the sample simultaneously while the device does not need to be increased in size.

In addition, since the back-side inspection optical system 130 uses the prism 133, the laser light source 131 and the scattered light detection optical system 1302 can be installed in a position separated from the table 111 and the stage 112. Thus, the defect inspection device can be compact. As described above, the laser light source 131 emits a laser beam that will be incident on the back surface 1002 of the sample 100 at an angle of approximately 30 degrees, and the scattered light detection optical system 1302 detects the light that has been scattered from the back surface 1002 at an angle of approximately 30 degrees.

The data processed by the front-side detected signal processing section 1431 and the data processed by the back-side detected signal processing section 1432 are transmitted to the integrated signal processing section 144 and processed thereby. The processed data is transmitted to the storage section 145 and stored therein as information on defects that are present on both surfaces of the sample 100. The data is also transmitted to the output section 146. The output section 146 outputs the information on the inspection results.

FIG. 6 shows an example of the information on the inspection results output from the output section 146. In this example, a distribution 602 indicates types of defects detected on the front surface 1001 of the sample 100, and a distribution 603 indicates types of defects detected on the back surface 1002 of the sample 100. The distributions 602 and 603 are displayed in a map format on a display screen 601. When a user specifies the size and type of a defect from a display area 604 on the screen, the user can visually recognize the specified type and size of the defect in each of the distribution 602 of the front surface 1001 and the distribution 603 of the back surface 1002.

In the present embodiment, the front and back surfaces 1001 and 1002 of the sample 100 are inspected simultaneously. Thus, the relative relationship between the position of a defect detected on the side of the front surface 1001 and the position of a defect detected on the side of the back surface 1002 can be identified. Therefore, the relative relationship can be used as effective information in order to manage a manufacturing process.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

What is claimed is:

1. A device for inspecting both sides of surfaces of a magnetic disk to detect defects thereon, comprising:
    a table unit that is capable of rotating and moving the magnetic disk with the magnetic disk mounted thereon;
    a front-side defect detecting section that optically detects a scratch and a defect that are present on a front surface of the magnetic disk mounted on the table unit;
    a back-side defect detecting section that optically detects a scratch and a defect that are present on a back surface of the magnetic disk;
    a processing section that processes an inspection result obtained by the front-side defect detecting section and an inspection result obtained by the back-side defect detecting section; and
    an output section that outputs the inspection results processed by the processing section,
    wherein the back-side defect detecting section includes:
        a laser light source that emits a laser beam;
        a light collecting section that collects scattered light by using a Fresnel lens, exclusive of regularly reflected light, the scattered light and the regularly reflected light being included in reflected light from the back surface of the magnetic disk that has been irradiated with the laser beam emitted by the laser light source;
        a first photoelectric converter that detects the scattered light that has been collected by the light collecting section; and
        an optical path changing section that reflects the laser beam emitted by the laser light source to change an optical path of the laser beam and thereby to direct the laser beam toward the back surface of the magnetic disk and that reflects the scattered light that has been collected by the Fresnel lens included in the light collecting section to change an optical path of the scattered light and thereby to direct the scattered light toward the first photoelectric converter.

2. The defect inspection device according to claim 1, wherein the optical path changing section includes a prism that has a reflective surface on which total reflection of light that has been incident thereon is made.

3. The defect inspection device according to claim 1, wherein the back-side defect detecting section further includes: a reflective plate that reflects, on the midway of the optical path of the reflected light from the back surface of the magnetic disk, the regularly reflected light to separate the regularly reflected light from the scattered light, the regularly reflected light and the scattered light being included in the reflected light; an imaging optical system that forms an image of the light regularly reflected on the reflective plate; and a second photoelectric converter that detects the optical image of the regularly reflected light, the optical image having been formed by the imaging optical system, and performs photoelectric conversion on the optical image.

4. The defect inspection device according to claim 1, wherein the Fresnel lens includes a first aspherical Fresnel lens that collects the scattered light from the magnetic disk and a second aspherical Fresnel lens that focuses the scattered light that has been collected by the first aspherical Fresnel lens.

5. The defect inspection device according to claim 1, wherein the front-side defect inspecting section includes:
    a laser light source that emits a laser beam;
    a light collecting section that collects scattered light by using a Fresnel lens, exclusive of regularly reflected light, the scattered light and the regularly reflected light being included in reflected light from the front surface of the magnetic disk that has been irradiated with the laser beam emitted by the laser light source;
    a third photoelectric converter that detects the scattered light that has been collected by the light collecting section;
    a reflective plate that reflects the regularly reflected light to separate the light from the scattered light, the regularly reflected light and the scattered light being included in the reflected light from the front surface of the magnetic disk;
    an imaging optical system that forms an image of the light regularly reflected on the reflective plate; and
    a fourth photoelectric converter that detects the optical image of the regularly reflected light, the optical image being formed by the imaging optical system, and performs photoelectric conversion on the optical image.

6. A method for inspecting both sides of surfaces of a magnetic disk to detect defects thereon, comprising the steps of:
    irradiating front and back surfaces of the magnetic disk mounted on a table with laser beams, the table rotating and moving in one direction with the magnetic disk mounted thereon;
    detecting a scratch and a defect that are present on the front surface of the magnetic disk by receiving and processing light that is reflected from the front surface that has been irradiated with the laser beam; and
    detecting a scratch and a defect that are present on the back surface of the magnetic disk by receiving and processing light that is reflected from the back surface that has been irradiated with the laser beam,
    wherein the step of detecting a scratch and a defect that are present on the back surface further includes the substeps of:
        causing the laser beam emitted by a laser light source to be reflected on a first surface of a prism to change an optical path thereof and direct the laser beam toward the back surface of the magnetic disk;
        irradiating the back surface of the magnetic disk with the laser beam whose optical path has been changed;
        causing light scattered from the back surface of the magnetic disk that is irradiated with the laser beam to pass through a Fresnel lens and to be focused;
        causing the scattered light that has passed through the Fresnel lens to be reflected on a second surface of the prism to change an optical path thereof and direct the scattered light toward a first photoelectric converter;
        detecting, by using the first photoelectric converter, the scattered light whose optical path has been changed;
        detecting, by using a second photoelectric converter, light regularly reflected on the back surface of the magnetic disk; and
        processing a signal obtained by causing the first photoelectric converter to detect the scattered light and a signal obtained by causing the second photoelectric converter to detect the regularly reflected light so as to detect a scratch and a defect that are present on the back surface of the magnetic disk.

7. The defect inspection method according to claim 6, wherein the regularly reflected light is reflected on a reflective plate so that the reflective plate changes an optical path of the regularly reflected light and separates the regularly reflected light from the scattered light, the regularly reflected light and the scattered light being included in the reflected light that are reflected on the back surface of the magnetic disk that has been irradiated with the laser beam.

8. The defect inspection method according to claim 6, wherein the step of causing light scattered from the back surface of the magnetic disk that is irradiated with the laser beam to pass through a Fresnel lens and to be focused further includes the steps of: collecting the scattered light by using a first aspherical Fresnel lens; and focusing, by using a second aspherical Fresnel lens, the scattered light that has been collected by the first aspherical Fresnel lens.

9. The defect inspection method according to claim 6, wherein the step of detecting a scratch and a defect that are present on the front surface includes the steps of: collecting the scattered light by using the Fresnel lens, exclusive of the regularly reflected light, the scattered light and the regularly reflected light being included in the reflected light from the front surface of the magnetic disk that is irradiated with the laser beam; detecting the collected scattered light by using a third photoelectric converter; causing a reflective plate to reflect the regularly reflected light so as to separate the regularly reflected light from the scattered light, the regularly reflected light and the scattered light being included in the reflected light from the front surface of the magnetic disk; forming an image of the regularly reflected light, the light being separated from the scattered light; detecting an image of the regularly reflected light by using a fourth photoelectric converter; and processing a signal obtained by causing the third photoelectric converter to detect the scattered light and a signal obtained by causing the fourth photoelectric converter to detect the image of the regularly reflected light.

* * * * *